(12) United States Patent
Hargrove et al.

(10) Patent No.: US 8,280,502 B2
(45) Date of Patent: Oct. 2, 2012

(54) METHOD AND APPARATUS FOR UTILIZING AMPLITUDE-MODULATED PULSE-WIDTH MODULATION SIGNALS FOR NEUROSTIMULATION AND TREATMENT OF NEUROLOGICAL DISORDERS USING ELECTRICAL STIMULATION

(75) Inventors: Jeffrey B. Hargrove, Bancroft, MI (US); Theodore J. Stokes, Lapeer, MI (US); Mary L. Esty, Chevy Chase, MD (US)

(73) Assignee: Cerephex Corporation, Bancroft, MI (US)

( * ) Notice: Subject to any disclaimer, the term of this patent is extended or adjusted under 35 U.S.C. 154(b) by 30 days.

(21) Appl. No.: 12/765,561

(22) Filed: Apr. 22, 2010

(65) Prior Publication Data
US 2010/0204750 A1 Aug. 12, 2010

Related U.S. Application Data

(60) Division of application No. 11/490,255, filed on Jul. 21, 2006, now Pat. No. 7,715,910, which is a continuation of application No. 10/357,503, filed on Feb. 4, 2003, now abandoned.

(60) Provisional application No. 60/353,234, filed on Feb. 4, 2002.

(51) Int. Cl.
*A61B 5/04* (2006.01)

(52) U.S. Cl. .................................. 600/544

(58) Field of Classification Search ............ 600/544, 600/545, 554, 561; 607/40, 42, 44, 45
See application file for complete search history.

(56) References Cited

U.S. PATENT DOCUMENTS

| | | | |
|---|---|---|---|
| 3,884,218 A | 5/1975 | Monroe | |
| 4,191,175 A | 3/1980 | Nagle | |
| 4,227,516 A | 10/1980 | Meland et al. | |
| 4,305,402 A | 12/1981 | Katims | |
| 4,315,502 A | 2/1982 | Gorges | |
| 4,612,934 A | 9/1986 | Borkan | |
| 4,651,145 A | 3/1987 | Sutter | |
| 4,719,922 A | 1/1988 | Padjen et al. | |
| 4,834,701 A | 5/1989 | Masaki | |
| 4,844,075 A | 7/1989 | Liss et al. | |
| 4,856,526 A | 8/1989 | Liss et al. | |
| 5,036,858 A | 8/1991 | Carter et al. | |
| 5,241,967 A * | 9/1993 | Yasushi et al. | 600/545 |
| 5,299,569 A | 4/1994 | Wernicke et al. | |
| 5,365,939 A | 11/1994 | Ochs | |

(Continued)

FOREIGN PATENT DOCUMENTS
WO WO-93/11831 A1 6/1993
(Continued)

*Primary Examiner* — Max Hindenburg
*Assistant Examiner* — Fangemonique Smith
(74) *Attorney, Agent, or Firm* — Reising Ethington P.C.

(57) ABSTRACT

A computing device-controlled system is described for the generation of amplitude-modulated pulse-width modulation (AMPWM) signals for use in treating neurological dysfunction via cranial neurostimulation, where the AMPWM signal is specifically designed to minimize the electrical impedance of the tissues of the head. A low-frequency carrier signal is determined for the AMPWM signal by measuring EEG activity at a reference site or sites, generally corresponding with the location of suspected brain dysfunction. Carrier signal frequency is variably related to critical frequency components of the EEG power spectral density, determined from statistical analysis of amplitudes and variability, and dynamically changed as a function of time to prevent entrainment. The AMPWM signal is presented to a subject via a plurality of neurostimulation delivery modes for therapeutic use.

22 Claims, 4 Drawing Sheets

U.S. PATENT DOCUMENTS

| | | | |
|---|---|---|---|
| 5,392,788 A | 2/1995 | Hudspeth | |
| 5,571,150 A | 11/1996 | Wernicke et al. | |
| 5,611,350 A | 3/1997 | John | |
| 5,720,744 A | 2/1998 | Eggleston et al. | |
| 6,016,449 A | 1/2000 | Fischell et al. | |
| 6,066,163 A | 5/2000 | John | |
| 6,081,743 A | 6/2000 | Carter et al. | |
| 6,246,912 B1 | 6/2001 | Sluijter et al. | |
| 6,350,275 B1 | 2/2002 | Vreman et al. | |
| 6,480,743 B1 | 11/2002 | Kirkpatrick et al. | |
| 2001/0003799 A1 | 6/2001 | Boveja | |
| 2001/0007950 A1 | 7/2001 | North et al. | |

FOREIGN PATENT DOCUMENTS

| | | | |
|---|---|---|---|
| WO | WO-01/26232 A2 | 4/2001 | |

* cited by examiner

METHOD AND APPARATUS FOR UTILIZING AMPLITUDE-MODULATED PULSE-WIDTH MODULATION SIGNALS FOR NEUROSTIMULATION AND TREATMENT OF NEUROLOGICAL DISORDERS USING ELECTRICAL STIMULATION

CROSS REFERENCE TO RELATED PATENT DOCUMENTS

This application is a divisional application of U.S. patent application Ser. No. 11/490,255, filed Jul. 21, 2006 now U.S. Pat. No. 7,715,910, which is a continuation application of U.S. patent application Ser. No. 10/357,503, filed Feb. 4, 2003 now abandoned, which is based upon and claims the benefit of priority from U.S. Provisional Application No. 60/353,234, filed on Feb. 4, 2002. The disclosures of the prior applications are hereby incorporated by reference herein in their entirety.

FIELD OF THE INVENTION

The present invention relates generally to the field of producing and applying electrical energy to the brain, and to the therapeutic uses of the electrical energy and an apparatus for administering the same. More specifically, the present invention relates to a system for controlling neurostimulation where the neurostimulation comprises an electrical signal whose characteristics minimize composite tissue impedances of the head, and more specifically yet, to a computer controlled system for automatic adjustment of neurostimulation signals related to critical frequency components of an acquired EEG signal, generally obtained at or near a region of suspected brain dysfunction.

The electrical activity, or EEG, of human brains has traditionally been used as a diagnostic marker for abnormal brain function and related symptomatic dysfunction. Often, traumatic disturbances such as mechanical injury, social stress, emotional stress and chemical exposure cause neurophysiological changes that will manifest as EEG abnormalities. However, disruption of this abnormal EEG activity by the application of external electrical energy, henceforth referred to as a neurostimulation signal, may cause yet further neurophysiological changes in traumatically disturbed brain tissues, as evidenced in an amelioration of the EEG activity, and hence are beneficial to an individual. Such therapeutic intervention has proven useful in pain therapy and in treating a number of non-painful neurological deficits such as depression, attention deficit disorder, and many others.

BACKGROUND OF INVENTION AND DESCRIPTION OF RELATED ART

In the 1960's and early 1970's, Robert Monroe of the Monroe Institute of Applied Sciences explored the effects of sound on the brain and discovered that he could produce a driving or entrainment of brain waves. Dr. Gerald Oster, a biophysicist, also investigating the effects of sound on the brain, discovered that pulsations called binaural beats occurred in the brain when tones of different frequencies were presented separately to each ear. The beat frequency equals the frequency difference between the two tones. Both Monroe and Oster began using electronic oscillators to provide tones with frequency, purity and intensity that can be precisely controlled.

U.S. Pat. No. 3,884,218 to Robert A. Monroe shows a method for inducing sleep by amplitude modulating a pleasing sound with a delta-rhythm signal that is referred to as an "EEG sleep signal." The '218 patent uses sound to induce sleep by creating a specific signal that coaxes the brain into a relaxed state. This signal chosen in the '218 patent is chosen based upon its proximity to signals that are strong during normal sleep.

U.S. Pat. No. 4,191,175 to Nagle shows a method and apparatus for repetitively "producing a noise-like signal for inducing a hypnotic or anesthetic effect . . . " by creating frequency bursts of digital pulses that are then passed through a pink noise filter to eliminate frequencies above a certain cut-off. The resultant signal is then passed through a band pass filter and used to drive an audible signal source.

An apparatus for electrophysiological stimulation is shown in U.S. Pat. No. 4,227,516 to Meland et al. in which a first signal above the delta-beta frequency range is modulated by signal within that range and applied to electrodes on the forehead of a user.

A learning-relaxation device of U.S. Pat. No. 4,315,502 has both lights for pulsing signals and sound means for a pulsing sound signal as well as a control means that can individually vary the light and sound signals.

U.S. Pat. No. 4,834,701 to Masaki shows a device similar to those used by Monroe and Oster with first and second generators with frequencies above 16 hertz and a frequency difference of 4 to 16 hertz sounded to lower the brain wave frequency of a user. The term "entrainment" began to be accepted for such devices: "This phenomenon, in which one regular cycle locks into another, is now called entrainment, or mode locking." (Gleick, Chaos: Making of a New Science 1987, Penguin Books, p. 293). An article entitled "Alpha Brain Waves & Biofeedback Training" in the December 1972 Popular Electronics show a system that uses a person's own EEG signal to modulate a tone generator which, in turn, then drives a speaker heard by the same person. The device allowed a person to "hear" his or her own brain signals in an attempt to voluntarily control the frequency. A similar device that allows a person to "see" his or her own brain waves is shown in an article entitled "Mind Power: Alpha" in the July 1976 Radio-Electronics.

U.S. Pat. No. 5,036,858 to John L. Carter, Harold L. Russell and Len Ochs shows the use of EEG electrodes attached to the head of the user along with an amplifier for determining a current brain wave frequency of a user, which is communicated to a computer processor. A new frequency is generated which is between the current brain wave frequency and a desired brain wave frequency and is within a predetermined range of the current brain wave frequency. This has become known as electroencephalographic entrainment feedback if it is used to "lock" the current brain wave frequency into a desired frequency.

U.S. Pat. No. 5,365,939 to Len Ochs provides a method of "exercising" the brain by using a device producing audio and visual stimulation to move a user's brain wave frequency back and forth between predetermined frequency levels.

In U.S. Pat. No. 6,081,743 to John L. Carter, Harold L. Russell, W. Daniel Vaughn and Robert R. Austin, a method for treating an individual is described by determining a brain wave frequency which corresponds to a highest evoked response of the individual, entraining the brain wave frequency to the brain wave frequency corresponding to the highest evoked response, and then maintaining the brain wave at that frequency for a predetermined length of time. The highest evoked response is described as the highest EEG response or the highest cerebral blood flow (CBF) of the individual or even some other measure.

Two patents in application at the time of the disclosure of the present invention relate to the present invention. In Application No. 20010003799 by Birinder B. Boveja an apparatus and method for adjunct (add-on) therapy utilizing an external stimulator is described to stimulate a cranial nerve according to a predetermined program.

In Application No. 20010007950 by Richard B. North et. al. a neurostimulation system and method is described that includes an implantable stimulator and patient interactive computer. Also, the '950 application requires patient interaction.

Prior methods of neurostimulation for therapeutic purposes have in many ways attempted to ameliorate brain functioning by providing the brain with electrical energy that is designed to be a reflection of the brain's own activity, often with the intent of modifying the brain electricity to follow, or entrain to, a desired frequency, range of frequencies, or relationship among frequencies, or alternately to target theoretically and empirically derived frequency states as a goal of training or therapy. However, little attention has been given to signal design for overcoming the complex and composite impedance presented by the tissues of the head. Such signals, when properly constructed, will limit attenuation of neurostimulation signals for improved effectiveness in patient treatment.

Regarding the concept of conductivity, it is known that the tendency of any conductive material to limit the flow of electrical charge, otherwise known as electrical current, is known as impedance. In general terms, attenuation of current flow is proportional to the magnitude of a material's impedance. The impedance of a substance is a function of its material and physical properties. Environmental factors, such as temperature, also influence the impedance of a material. Most significant to the disclosure of the present invention is the relationship between impedance of a material and the frequency of the electrical signal being conducted through the material.

In its most fundamental terms, three electrical effects govern impedance: resistance, capacitance and inductance. Resistance is a fundamental form of impedance that is constant in time. Therefore, the frequency of a signal has no effect on resistance. However, both capacitive and inductive effects are functions of frequency. Inductive reactance, the formal name for impedance due to inductance, is proportional to frequency. Thus, the higher the frequency of a signal is, the higher will its corresponding inductive reactance be. Capacitive reactance, the formal name for impedance due to capacitive effects, is inversely proportional to frequency. Thus, as a signal's frequency increases, the impedance of a material due to capacitance decreases. For very high frequencies, capacitive reactance can become very small, and the resulting attenuation of the flow of current will be correspondingly less.

The head is comprised of a series of tissues that can be approximately thought of as composite layers surrounding the brain. Specifically, these layers of tissue include the dermal layers of the scalp, the skull, the meninges, the cerebral spinal fluid that bathes the brain, and the brain itself including both healthy tissues and unhealthy tissues such as lesion matter forming in the region of damage. The impedance of the tissues of the head is known to be complex in nature, that is, they have both a resistive component and a capacitive component. Thus, the overall impedance of these tissues will be a function of signal frequency because of capacitive reactance, and an electrical circuit model of these impedances must account for this fact. Because of the nature of this impedance, a higher frequency signal will pass through the tissues with much less attenuation.

SUMMARY OF THE INVENTION

The present invention is based on the discovery that certain neurostimulation signals can provide an optimal effect on the tissues of the brain, while eliminating conscious patient perception of the signal.

Thus, the invention is directed towards a method of treating one or more neurological dysfunctions. The method comprises taking a first measurement of the EEG of a subject afflicted with at least one type of the neurological dysfunction in order to obtain EEG results and evaluating the EEG results to determine whether any region of the subject's brain possesses irregular activity as compared to other regions of the subject's brain. A determination of a dominant frequency is separately made for each of the regions of the subject's brain that possess irregular activity by examining the EEG results from each the regions of the subject's brain that possess irregular activity. Finally, the method comprises an administration of an anti-neurological dysfunction therapy to the subject. The anti-neurological dysfunction therapy comprises inducing a neurostimulation signal directed to the regions of the subject's brain that possess irregular activity for a time sufficient to normalize the EEG of the regions of the subject's brain that possess irregular activity. Additionally, further EEG measurements from the regions of the subject's brain that possess irregular activity are monitored during the administration of the therapy and the neurostimulation signal is adjusted based on any detected changes in the additional EEG measurements.

The invention is also directed to an apparatus for neurostimulating a subject. The apparatus comprises a computing device that is operatively coupled to a neurostimulator, and a series of EEG sensors that are coupled to the neurostimulator. The EEG sensors are configured (1) to be attached to the subject, (2) to monitor EEG results of a subject, and (3) to administer neurostimulation signals to the subject. Additionally, the EEG sensors preferably comprise at least one positive contact, at least one negative contact, and at least one ground contact.

In accordance with the disclosure herein, an object of the present invention is to generate an electrical signal for the purposes of neurostimulation that also minimizes the effect of tissue impedance to the improved flow of electrical energy to body tissues.

It is a further object to pass extremely low power signals with minimal attenuation into subjects who possess a high sensitivity to neurostimulation signals.

It is a further object to use an electrical signal referred to as an amplitude-modulated pulse-width modulation (AMPWM) signal. An AMPWM signal is characterized by a high frequency component that is modulated by a low frequency carrier for stimulation purposes.

It is a further object to use pulse-width modulation and/or amplitude control of the high frequency component of the AMPWM signal in order to control the electrical energy level present in a neurostimulation signal.

It is a further object of the present invention to use an AMPWM signal in neurostimulation in order to disentrain an EEG signal. Disentrainment involves the prevention of the EEG signal from locking into a particular frequency or frequency range, and to cause, rather, the redistribution of EEG spectral energy. Additionally, it is an object of the present invention for the AMPWM signal to not maintain a given frequency for a period of time sufficient to cause dysfunctional entrainment such as that which occurs in an epileptic seizure.

A further object of the present invention is to provide a means of constantly assessing power spectral density or other frequency related statistics of EEG signals, and using the frequency related statistics from the EEG signals to manage the low frequency component of an AMPWM neurostimulation signal so as to prevent entrainment to any specific frequency, and to distribute energy uniformly.

A further object is to provide a means of entraining EEG signals by controlling the low-frequency component of an AMPWM neurostimulation signal.

A further object is to provide a means of controlling the low frequency component of an AMPWM signal so that the frequency of the low frequency component is determined as a function of either a constant offset in time or a frequency analysis driven offset determined as a function of time.

Another object of the present invention is to provide a means of delivering a neurostimulation signal to regions of the scalp corresponding to suspected regions of brain dysfunction by inducing the neurostimulation signal into EEG sensors that are concurrently used for measurement of EEG signals.

Another object of the present invention is to provide neurostimulation in which electrical currents are passed through suspected regions of brain dysfunction through EEG sensors which are placed in a manner so that the region of the brain of the subject in which a dysfunction is located is in the area of placements of EEG sensors.

Another object is to provide for the utilization of an AMPWM signal for delivery of neurostimulation through a photic means, such as rapid pulsing of light-emitting diodes, in which the light intensity is controlled by pulse width modulation of the high frequency component of the AMPWM signal.

Another object of the present invention is to provide a means of modifying the low-frequency component of an AMPWM signal to relate to frequency components of EEG signals, the means being accomplished by any number of frequency analysis techniques.

Another object is to provide a system for neurostimulation that includes a means for acquiring EEG signals from a subject, analyzing the EEG signals for frequency components and generating an AMPWM signal which is delivered to the subject for either the disentrainment or the entrainment of EEG activity of the subject for therapeutic purposes.

Another object is to provide a means of determining suspected regions of brain dysfunction in a subject by acquiring EEG data from a number of scalp sites of the subject, analyzing the EEG data for frequency components and assignment to standard bands of EEG (e.g. delta, theta, etc.), determining the electrical energy in each of the standard bands by analysis in order to determine a statistic that is a function of total power in the band to include but not limited to sum of amplitude, or root-mean-square, or root square summation; and variability to include but not limited to variance or standard deviation, and using the statistic magnitude as a function of EEG frequency range as an indicator of brain dysfunction.

A further object is to provide for an enhanced means of determining brain dysfunction related to patient symptoms by measuring sites correlating to known systemic functions (e.g. pain, speech, movement) and performing the previously described statistical analysis.

A further object is to provide a means of using the statistics obtained from the previously described statistical analysis to create a visual graphic corresponding to regions of the brain for comparative purposes.

A further object of the present invention is to provide a means of delivering neurostimulation by using more than one EEG amplifier for multi-site neurostimulation, and wherein an AMPWM signal is delivered either via photic means or directly to suspected regions of brain dysfunction via EEG sensors operatively coupled with an EEG amplifier.

A further object of the present invention is to provide methods of controlling neurostimulation signal parameters such as signal energy level, frequency of the low frequency component of an AMPWM signal, phase offset of multiple signals, start time and duration through a user interface.

A further object is to provide for selection of a neurostimulation delivery mode.

A further object is to provide a method of assuring EEG lead interface integrity, for both EEG acquisition purposes and neurostimulation purposes, by testing using an algorithm to analyze a measure EEG signal to determine lead interface integrity. This algorithm detects random electrical noise, which is a sign of poor interface integrity.

A further object of the present invention is to provide neurostimulation for other purposes of enhancing brain activity, such as brainwave training.

A further object is to provide a means of correlating EEG data to observed events and/or perceived events by provision of an interface control for marking data either by a patient or a clinician during neurostimulation.

These and other objects, advantages and features of this invention will be apparent from the following description taken with reference to the accompanying drawings, wherein is shown a preferred embodiment of the invention.

DETAILED DESCRIPTION OF THE PREFERRED EMBODIMENTS

Figure 1:
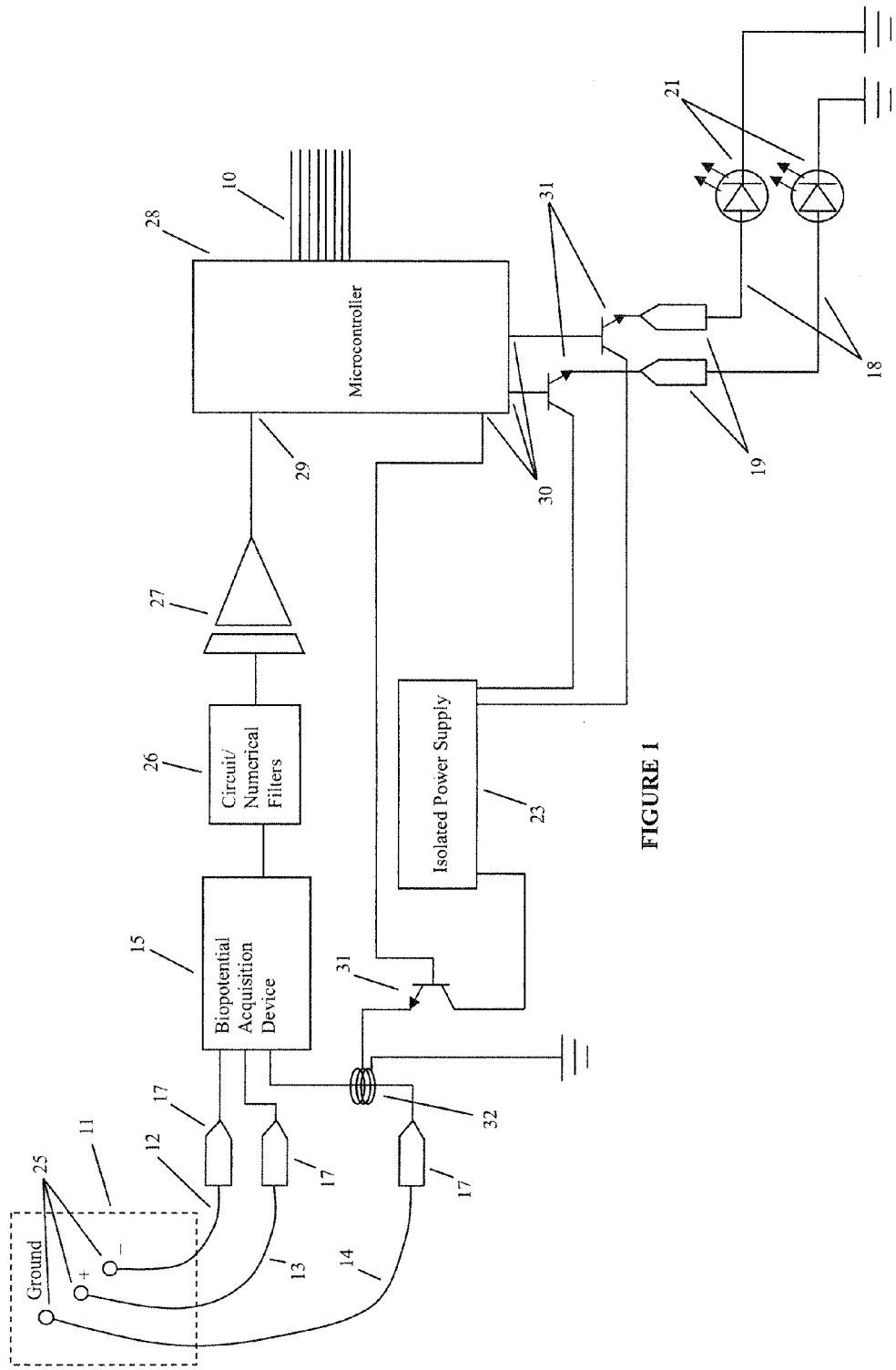
FIG. 1 illustrates a view of the apparatus.

The present invention is directed towards a method and an apparatus suitable for the treatment of neurological dysfunctions.

The term "optical unit" is intended to define an apparatus that is used on or in close proximity to the eyes. By close proximity, it is meant a distance from the eyes of a subject that is effective for the transmittal of a light pulse into the eyes of the subject. Preferably, close proximity will not exceed one foot in distance from the subject. The structure of the optical unit may be worn on the face of the patient, such as optical device or goggles, or it may be located in a separate structure, such as a stand that is held near the face or even a hand-held mask. Further, the optic unit may be placed at an angle to the eyes of the subject. Additionally, the optic unit may be positioned behind the subject and use mirrors or other reflective devices (such as a white wall) to reflect the light pulse into the eyes of the subject. However, in no way is this definition intended to limit the ultimate structure the optical unit may take.

The term "neurological dysfunction" is intended to define a group of disorders in which one or more regions of a subject's brain operate at frequencies which are different from the predetermined frequency for that region of the brain or from the predetermined frequencies of the other regions of the subject's brain. Examples of neurological dysfunctions include traumatic brain injury, post traumatic stress disorder, post stroke paralysis, post traumatic brain injury paralysis, cerebral palsy, headache, depression, post chemotherapy cognitive, mood and fatigue disorder, fibromyalgia, memory loss, coma, attention deficit disorder, etc. However, the present invention is not to be construed as being limited to the treatment of these listed examples.

The term "irregular activity" is intended to define the EEG frequency of an region of the subject's brain which does not match the predetermined EEG activity of the remaining regions of the subject's brain. Additionally, the term "irregular activity" is also intended to define an EEG frequency of an region of the subject's brain that matches the EEG activity of the remaining regions of the subject's brain, but with a high degree of variance. Irregular activity is determined by analyzing the frequency bands of the region of the brain being investigated and identifying either a higher band amplitude or a lower band amplitude than is predetermined for that region. Examples of potential irregular activity include amplitude abnormalities in which the measured peak-to-peak microvolts is over 14 microvolts (abnormally high) or in which the measured microvolts is under 5 volts from peak-to-peak (abnormally low) or possesses a standard deviation of over 3 microvolts. However, these are examples only. One of ordinary skill would recognize what a proper benchmark would be for each subject.

The term "neurostimulation signal" is intended to define a signal transmitted by the neurostimulator to a subject for the purpose of normalizing the brainwave activity of regions of the subject's brain that possess irregular activity. The neurostimulation signal is determined on a subject by subject basis and is changed in relation to a shift in the region's dominant frequency. There is typically a reduction in variability as EEG changes occur. This is evidenced by a shift in the dominant frequency more towards the typical frequencies and amplitudes that were predetermined for that region of the subject's brain.

The term "normalization" is intended to define the result of the administration of a neurostimulation signal to regions of the subject's brain that correspond to the regions of the subject's brain that possess irregular activity. The neurostimulation signal is intended to "normalize" or adjust the brainwave frequency of the regions of the subject's brain that possess irregular activity to reflect the predetermined frequency of the region of the subject's brain that is being treated.

The term "dominant frequency" is intended to define the frequency in the EEG measurements taken from an area of the subject's brain that possesses the highest voltage amplitude.

The present invention is directed towards the alleviation of symptoms of neurological disorders caused by irregular EEG activity in a subject's brain. The alleviation of the symptoms is accomplished by administering a neurostimulation signal to the regions of the subject's brain that are related to those regions of the subject's brain that possess irregular activity. These related regions of the subject's brain can include regions that possess irregular activity, or other regions of the brain. One of skill in the neurological arts would recognize which regions of the brain are interrelated with other regions of the brain.

For example, in one method of choosing the treatment sites, the choice is determined by the regions of EEG-slowing specific to an individual, regardless of the diagnosis. In this method, it is the presence and pattern of EEG-slowing at any of the standard neurological 10-20 sites (as selected by the International 10-20 EEG Site Placement Standard) that is the indication of the appropriateness of an region of the brain for treatment. The EEG-slowing pattern also determines where on the scalp electrodes will be placed for treatment.

Because EEG slowing that is associated with fatigue, poor short-term memory, and attention problems is likely to involve functional deficits in the left frontal lobes of the brains, placing electrodes on any of the following sites is a reasonable directive: FP1, F7, F3, C3, F1, AF7, F5, AF3 and possibly temporal sites, T3 & T5 (according to the International 10-20 EEG Site Placement Standard). The amplitudes and standard deviations from the image data determine the order of treatment for these sites.

The imaging data is preferably gathered by sequentially recording from each of 21 sites. These data are preferably processed through a Fast Fourier Transform (FFT) computation which produces quantitative data that shows the average microvolts and the standard deviation for each frequency component of the EEG signal at each site. A preferred method of treatment is to identify those sites that have the highest standard deviation as shown in the FFT results and treat them first. Treatment can be accomplished by placing two pairs of electrodes (one positive and one negative comprise a pair) on each of the four sites having the highest measured amplitudes.

It is the unique EEG pattern of the individual, however, that is the key to the most efficient treatment. The determination of treatment sites applies to any diagnostic category of neurological dysfunction and the determination is individualized by the quantitative data from each individual's brainwave data. Therefore, it is not possible to specify a standard set of sites for any given, or all, diagnostic categories. However, there is a broad diagnostic classification called EEG-slowing and that this category can permit the selection of predetermined sites from which to direct the treatment of choice. Therefore, given the above information one of ordinary skill would understand how to select a region of the brain for treatment on a subject by subject basis.

The neurostimulation signal is administered by modulating a high frequency component, which can be further pulse-width modulated for control of the energy level, with a low frequency carrier. It is the preferred intent of the present invention to "disentrain" the brain's electrical activity, that is, to not target or lock into a particular frequency, but rather to redistribute existing energy to all frequencies in the normal spectra of the brain EEG in a typically uniform manner. However, the present invention does not preclude the utilization of the neurostimulation signal for the purposes of entrainment.

The present invention also embodies a method of focusing a neurostimulation signal directly on a suspected dysfunctional region of the brain. This is possible because tissue impedances are minimized by the design of the neurostimulation signal. The neurostimulation signal possesses a greater ability to directly reach damaged regions of the brain rather than simply following the outer-most tissues around the scalp and thereby bypassing the damaged region of the brain. Another advantage is achieved by inducing the neurostimulation signal directly into EEG sensors. This advantage is that the neurostimulation signal can be strategically placed to present a conduction path through the damaged region of the brain, while concurrently measuring the EEG signal at the dysfunctional regions, thus providing a direct link between the measured EEG signals and the neurostimulation signals being delivered directly to the dysfunctional region.

A method for treating a subject with the method of the present invention preferably includes the generation of an electrical neurostimulation signal characterized by a high frequency pulse train modulated by a low frequency carrier signal. A means of providing for variable levels of electrical power may be accomplished by using either pulse width modulation of the high frequency pulse train, as in the preferred embodiment of the present invention, or variable amplitudes of the same pulses. Preferably, the frequency of the high frequency pulse train is at least one order of magnitude greater than the frequency of the low frequency carrier signal. It is preferred that the high frequency pulse be in the range of 43 to 1,000,000 hertz. It is more preferred that the high frequency pulse be in the range of 1,000 to 100,000 hertz. It is even more preferred that the high frequency pulse be in the range of 10,000 to 20,000 hertz. It is most preferred that the high frequency pulse be 15,000 hertz.

The low frequency carrier signal is variably related to critical frequency components of the EEG power spectral density, determined from statistical analysis of amplitudes and variability. The low frequency carrier signal is determined from information obtained by measuring EEG activity at a reference site or sites that generally corresponds with the location of suspected brain dysfunction, and the low frequency carrier signal is dynamically changed as a function of time to prevent entrainment. This is performed by changing the frequency offset (as described below) at predetermined time intervals. It is preferred that the low frequency carrier signal be typical of a brainwave EEG. It is more preferred that the low frequency carrier signal be in the range of 1-42 hertz.

The combination of (1) the high frequency pulse train as it is modulated by (2) the low frequency carrier signal, henceforth referred to as an AMPWM signal, provides a means of minimizing the effect of tissue impedances of the head. However, no limitation of the present invention to AMPWM signals alone is intended by this abbreviation. Any signal that possess both (1) and (2) as defined above is intended to be encompassed by the present invention.

In general, as will be discussed in greater detail in subsequent sections of this disclosure, the electrical impedance of tissues of the head decreases with increased electrical signal frequency. Thus, the high frequency pulse train component of the AMPWM signal passes through the head tissues with less attenuation than the low frequency carrier signals typically used in already known neurostimulation methods. Further, the low frequency carrier signal component of the neurostimulation signal in essence serves to turn on and off the high frequency signal component with a frequency that is generally related to the range of frequencies present in an EEG signal. Thus, the low frequency carrier signal component may be produced at frequencies commonly used for therapeutic purposes in neurostimulation devices, such as entrainment or disentrainment.

Some neurological dysfunctions that may be treated by the present invention include traumatic brain injury, post traumatic stress disorder, post stroke paralysis, post traumatic brain injury paralysis, cerebral palsy, headache, depression, post chemotherapy cognitive, mood and fatigue disorder, fibromyalgia, memory loss, coma, attention deficit disorder, etc. However, this list is not intended to be exclusive.

The method preferably comprises taking a first measurement of the EEG of a subject afflicted with at least one type of the neurological dysfunction in order to obtain EEG results and evaluating the obtained EEG results to determine whether any region of the subject's brain possesses irregular activity as compared to other regions of the subject's brain. It is preferred that the subject be a mammal and, more preferably, a primate. It is most preferred that the subject be a human being. It is also preferred that the irregular activity be determined by comparing the EEG signals from a region of the subject's brain with the EEG signals from the remaining regions of the subject's brain. It is also preferred that the EEG signals are obtained from more than one region of the subject's scalp. It is even more preferred that the EEG signals be obtained from at least 21 regions of the subject's scalp that correspond to 21 regions of the subject's brain. It is preferred that the regions be selected according to the International 10-20 EEG Site Placement Standard.

A determination of a dominant frequency of the subject's brain is made from the evaluating the EEG results from the regions of the subject's brain that possess irregular activity. Preferably, the evaluation involves the correlation of the EEG signals into a graphic image of the subject's brain. Even more preferably, the graphic image is evaluated and new EEG signals from the subject's brain are taken in order to ensure that the first EEG signals were accurate and in order to determine a dominant frequency from the regions of the subject's brain that have been confirmed as possessing irregular activity.

Finally, the method comprises an administration of an anti-neurological dysfunction therapy to the subject. The anti-neurological dysfunction therapy comprises inducing a neurostimulation signal directed to the regions of the subject's brain that possess irregular activity for a time sufficient to normalize the EEG signals of the regions of the subject's brain that possess irregular activity.

It is preferred that the time be between one second and one hour. It is more preferred that the time be between 1 and 30 minutes. It is even more preferred that the time is between 1 minute and 10 minutes. It is even more preferred still that the time be between 1 minute and 3 minutes. It is still more preferred that the time be between 1 second and 30 seconds. It is most preferred that the time be between 1 second and five seconds Additionally, further EEG signal measurements from the regions of the subject's brain that possess irregular activity are monitored during the administration of the therapy and the neurostimulation signal is adjusted based on any detected changes in the additional EEG signal measurements. The normalization of the EEG signals from the regions of the subject's brain that possess irregular activity results in an alleviation of the symptoms of the neurological disorders.

The neurostimulation signal comprises a carrier frequency which comprises the dominant frequency and the frequency offset. It is preferred that the frequency offset be between −10 and 20 hertz.

It is preferred that the normalization of the regions of the subject's brain that possess irregular activity result in these regions transmitting EEG signals which are close to the predetermined frequency and amplitude expected for those regions of the subject's brain. It is even more preferred that these regions transmit EEG signals at the predetermined frequency and amplitude expected for those regions of the subject's brain after the treatment.

The subject may require multiple exposures to the method in order to achieve an alleviation of the symptoms he or she suffers from the neurological dysfunctions. It is preferred that the multiple exposures remain in the range of 1 to 40 exposures. However, more exposures are permitted, if required. It is more preferred that the exposures remain in the range of 10 to 30 exposures. It is more preferred that the exposures remain in the range of 5 to 10 exposures. Additionally, it is preferred that a repeated use of the method be avoided within 24 hours of a previous use of the method. However, if required, it is possible to treat more than one region of the subject's brain (if more than one region of the subject's brain possesses irregular activity) in one treatment session.

Additionally, the subject may be medicated, sedated, or unconscious during the administration of the method. However, it is preferred that the subject be in none of these conditions.

Regarding the application of the neurostimulation signal itself, after the identification of regions the subject's brain which possess irregular activity, neurostimulation treatment is accomplished by placing EEG sensors in an arrangement that allows for the measurement of the EEG activity from the dysfunctional region, as well for providing a successful delivery of current from the EEG sensors into a system ground. The computer-controlled system in the preferred embodiment of the present invention acquires EEG signal data from the sensor sites and conducts an analysis of the EEG signal data to determine the frequency of the low frequency carrier signal component of the AMPWM signal.

The AMPWM signal can be transmitted to the subject through a plurality of neurostimulation delivery modes. In a preferred embodiment of the present invention the preferred mechanism of delivery is accomplished by inducing the AMPWM signal into the EEG sensors through inductive coupling. Another preferred mechanism is to use the AMPWM signal to drive a light-generating component, such as a light emitting diode, to provide a photic stimulation signal that may be delivered to the patient through the optic nerve.

Another preferred embodiment involves the simultaneous use of stimulation delivery by inducing the AMPWM signal into the EEG sensors through inductive coupling and drive a light-generating component, such as a light emitting diode, to provide a photic stimulation signal. In essence, this is a combination of previously discussed embodiments.

Lastly, it is preferred that EEG leads be placed on the scalp regardless of what stimulation method is used because the apparatus and method preferably measures EEG during stimulation delivery, and uses these EEG measurements to drive neurostimulation signal parameters.

In a preferred embodiment of the present invention, delivery mode is selectable to account for different levels of sensitivity and tolerance in patients. It is also possible to completely automate the process of transmitting the neurostimulation signal and the monitoring of the EEG signal data from the EEG sensors.

As stated above, it is preferred that the EEG signals from the subject be measured at typically 21 different scalp locations and it is preferred that power spectral density computations are performed on the obtained EEG signals. These computations break the measured analog EEG signals into frequency domain data such as a Fourier series of discrete frequency components, which is limited to 1-42 Hertz (greater signal components exist and could be utilized, but the 1-42 Hertz range is typically considered clinically useful). However, other methods of obtaining the frequency domain data are acceptable (such as the use of wavelet analysis).

In analyzing EEG signal data, frequency bands are commonly used. For example, the "delta" band is typically 1-4 Hertz, the "theta" band is 5-7 Hertz, and so on. For each site, the total amplitude associated with each discrete frequency component is assigned to proper bands, providing a measure of the EEG band energy for each of the aforementioned sites.

From this, a graphic "image" is generated where colors represent amplitudes. From this image, the clinician can see EEG band activity related to regions of the brain, and based on clinical knowledge, can determine if a region has unusual or abnormal activity.

Accordingly, the neurostimulation phase of the process (i.e. treatment) is administered to correct regions of abnormal activity. The administration of the neurostimulation signal is preferably performed after the imaging process described above is completed. The clinician preferably applies EEG sensors to regions of the scalp that relate to the regions of suspected dysfunction and the EEG signal data is preferably re-measured for a period long enough to provide power spectral density data (as in the imaging process). The frequency domain data is then sorted, and the frequency that exhibits the highest amplitude is designated the "dominant frequency". According to clinician chosen stimulation time and frequency parameters, a neurostimulation signal is generated that has a "carrier frequency" that is determined by the formula:

CARRIER FREQUENCY=DOMINANT FREQUENCY+FREQUENCY OFFSET

The parameters the clinician uses are (1) stimulation intensity, (2) the times that the stimulation signal is turned on in the treatment cycle (as well as the number of times), (3) the duration that each stimulation signal is turned on, the leading frequency of each stimulation event, and (4) the phase offset of each stimulation event. Intensity is defined by the pulse-width-modulation duty cycle, and ranges from 0 (no "on-time") to 100% (no "off-time"). Thus, an intensity of 50% would have a duty cycle such that "on-time" is equal to "off-time" in each pulse cycle. The number of stimulation cycles and the times that the stimulation turns on is entirely clinician driven. However, it is preferred ranges that the stimulation cycles range between 1 stimulation event up to 50. It is preferred, however, that no more than 20 different stimulation events be used per session. The preferred leading frequency is already defined to range between −10 and 20 Hz. Preferred Phase offset ranges from −180 to 180 Hz.

In this formula, "frequency offset" is preferably selected from the range of −40 to 40 Hertz and more preferably from −10 and 20 Hertz.

The offset is chosen by clinical experience, therefore, one of ordinary skill in the art would recognize how to choose an offset. However, the clinician generally picks the largest offset (i.e., +20 Hz) to see if a response is elicited. If no response is elicited, lower offsets will be tried until a response is obtained. The clinician's choice of parameter values is typically driven by a selection of choices that cause the subject to react, but yet do not cause an "over-reaction" which is an adverse effect characterized by short-term fatigue, headache, etc All of the preferred neurostimulation parameters to be considered are defined below. Values of these parameters are chosen based on clinician experience, and are selected in a manner that is meant to cause a reactive therapeutic effect without causing the subject to over-react. The selection of these values is further driven by subject condition and symptomatic presentation. For example, a subject with mild traumatic brain injury may be able tolerate a longer (in duration) than average stimulation application without suffering an adverse effect. However, a subject with Fibromyalgia with severe fatigue may only tolerate a very short (in duration) stimulation burst at the lowest intensities possible. The ranges of values for these parameters are provided for the clinician to choose based on experience, patient condition and symptomatic presentation, thus no preferred or optimal values exist. These parameters include:

Intensity—This is a measure of the pulse width modulation signal's duty cycle. This provides a variation on the time-averaged current delivered to the stimulation mechanisms (i.e. the EEG lead inducing circuit and the photic stimulators).

Duration—This is a measure the time in seconds that a neurostimulation event (i.e. a period of stimulation signal output) lasts. This can range from 1 second to 1,200 seconds in the preferred embodiment.

Start Time—This is the time in seconds after the beginning of a neurostimulation treatment session begins when a neurostimulation event starts to occur. There is no specific limitation on this, that is, the start time could begin at any time after the treatment session begins. Before the start time occurs, the system is simply measuring EEG and this could, theoretically, go on indefinitely.

Leading Frequency and Phase Offset are previously defined.

By adding the frequency offset to the dominant frequency, a carrier frequency is created that is always different than the dominant frequency. This neurostimulation signal is then either induced in the EEG sensors attached to the subject's scalp or the neurostimulation signal is used to drive light emitting diodes for photic stimulation purposes. The duration of the signal, along with other parameters (as described above) such as intensity and phase offset (in the case of LEDs for photic stimulation—a phase offset causes the LEDs to flash out of synchronization with each other) are determined by the clinician's chosen treatment protocol.

Figure 2:
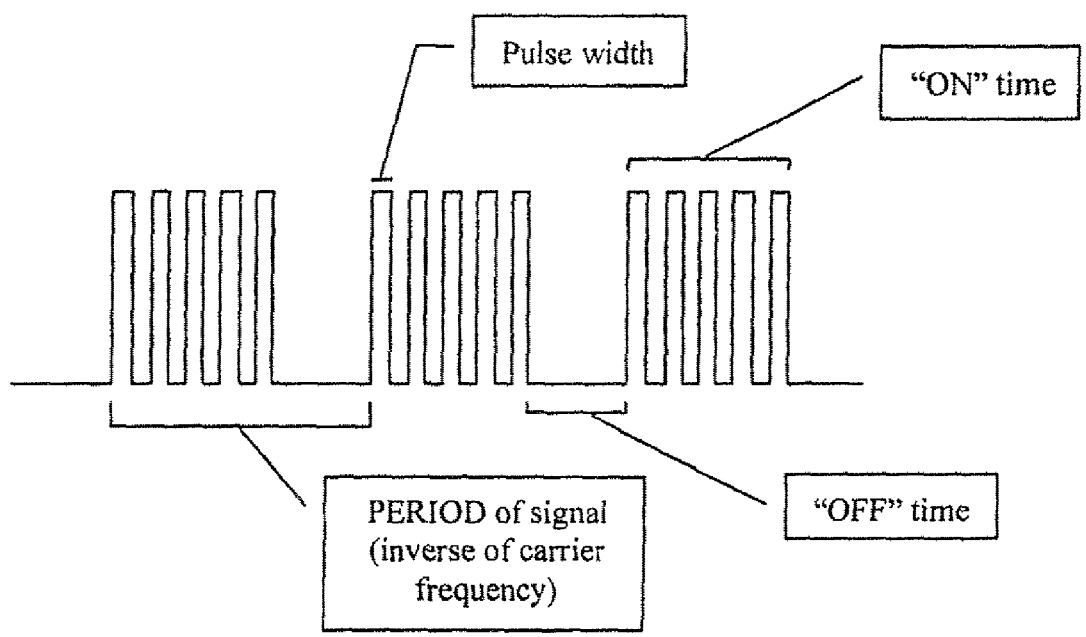
FIG. 2 illustrates a graphic representation of the neurostimulation signal. It is a representation for illustrative purposes only and it is not intended to limit the scope of the signal used in the present invention in any way.

As described above, the neurostimulation signal can be an amplitude modulated pulse-width modulation signal. A graphic representation of the signal is shown in FIG. 2. In other words, the carrier frequency simply turns an electric signal on and off in a way that a square-wave pulse train is generated with a frequency equal to the carrier frequency. Thus, in a period (period=1/frequency) of this pulse train, there will be an amount of time that the electric signal is "on" and an amount of time when the signal is "off" (see FIG. 2). During the time that the carrier signal is "on", the electricity is further pulsed at a very high frequency. A pulse width modulator is used to control this high frequency pulsing. By varying the pulse width, the average current applied is varied. This is what varying the "intensity" means. With a very low duty cycle, there is very little average current and thus the neurostimulation signal has very low intensity. Conversely, a higher duty cycle delivers more current and thus the intensity increases. A 100% duty cycle means that there is no "high frequency off time", and thus the entire neurostimulation signal is a simple square wave pulse train with frequency equal to the carrier frequency.

Figure 3:
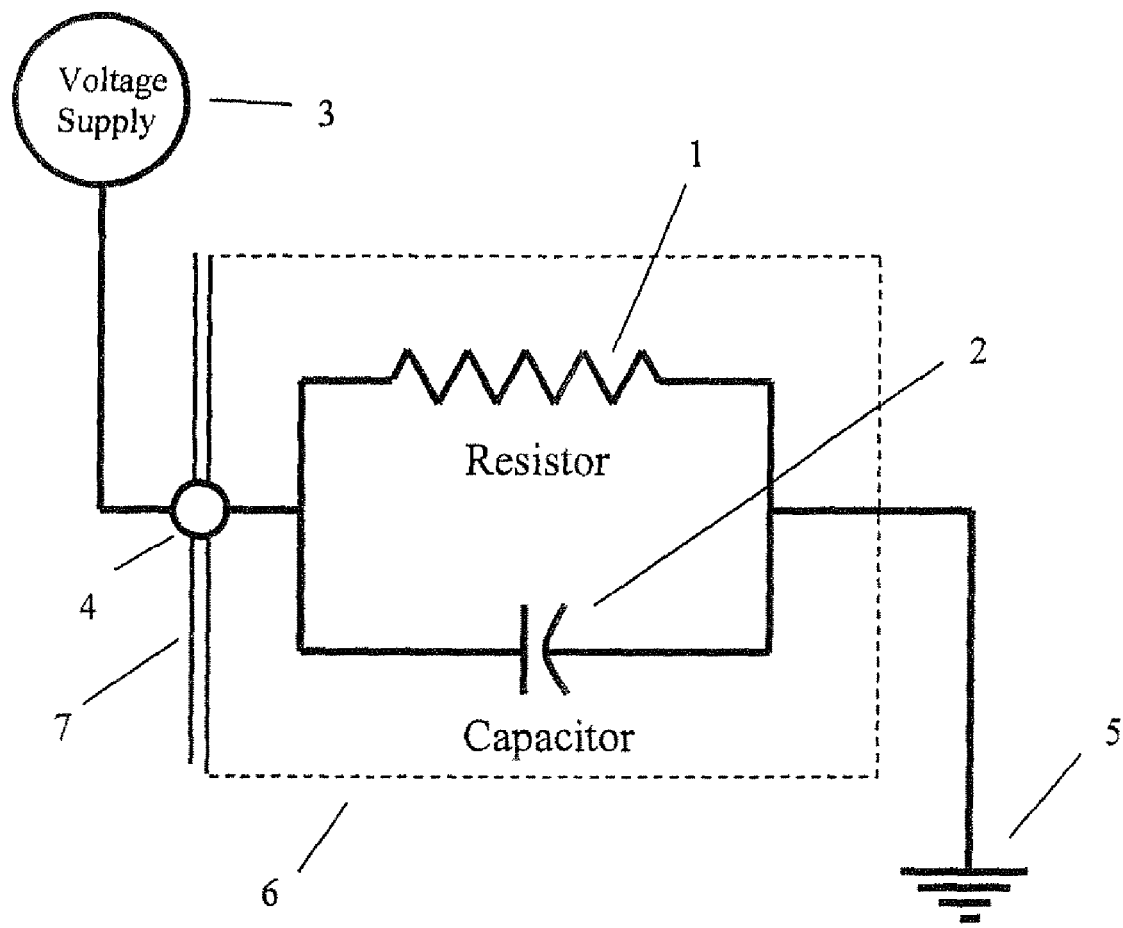
FIG. 3 presents a model of the apparatus of the present invention in regards to tissue impedance.
Figure 4:
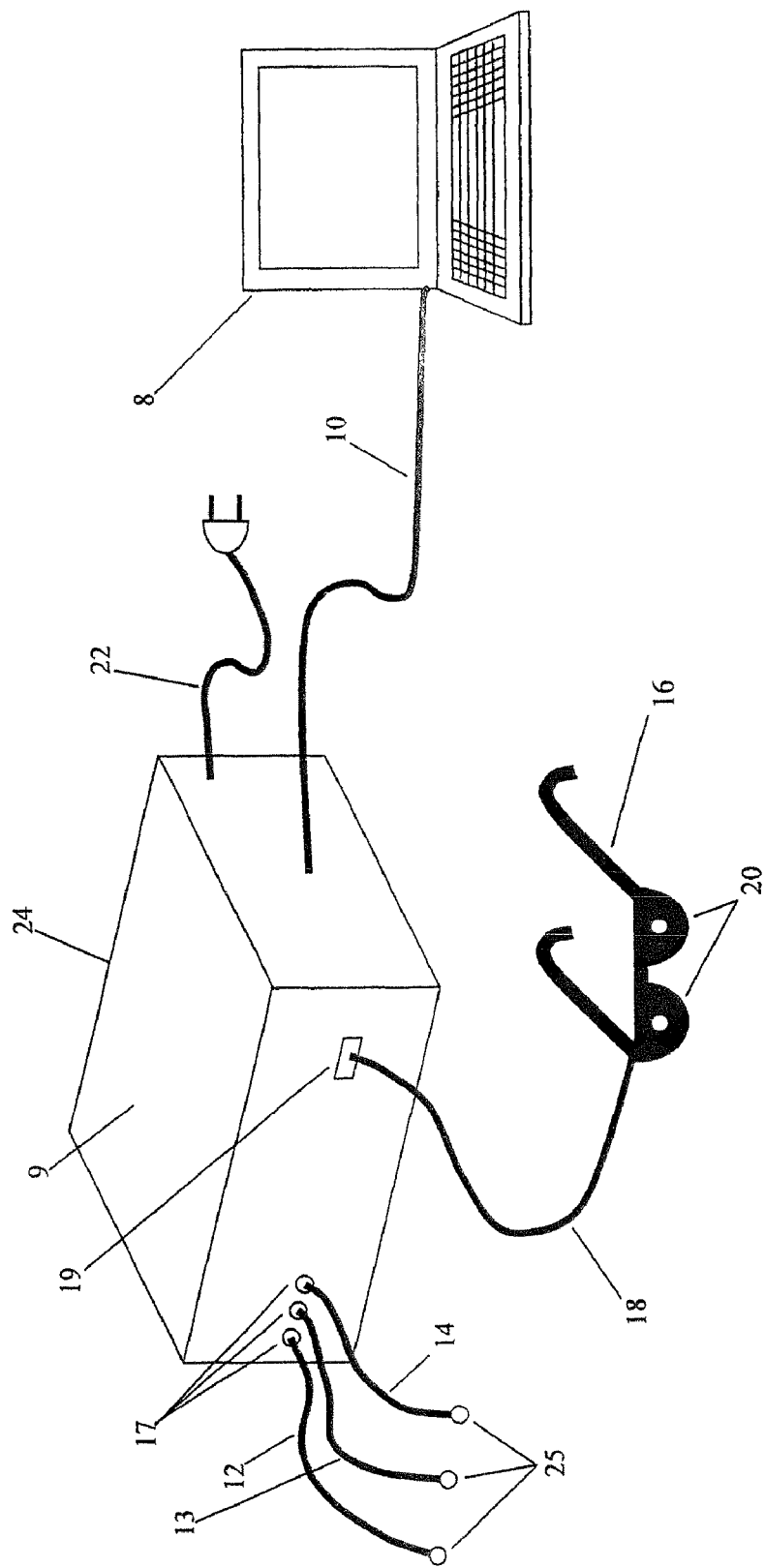
FIG. 4 illustrates another view of the apparatus.

Regarding the apparatus, FIG. 3 presents a model of the apparatus of the present invention. In FIG. 3., tissue impedance 6 is represented by a parallel combination of a simple resistor 1 and a simple capacitor 2. A voltage source 3 provides electricity at a supply electrode 4 interfaced at a subject's skin 7, with the electricity passing through the tissue impedance 6 and ultimately being returned to a common ground 5 potential. Following fundamental circuit analysis, the equivalent impedance ($Z_{EQUIVALENT}$) of the circuit is given by the formula:

$$Z_{EQUIVALENT} = \frac{R}{1 + 2\pi fRC}$$

In this formula, the resistance is given by the nomenclature R, capacitance by C and frequency by f. This equation clearly shows that as the frequency of the signal increases, the overall impedance of the system decreases despite the level of impedance from the resistor 1 being constant. Although the impedances of the composite tissues of the head are considerably more complex and require a far more sophisticated model to accurately describe current flows, this model provides a simple analogy and approximately describes the effect, and is a fundamental basis for the disclosure of the present invention.

The effects of applying electrical energy to brain tissues, the electrical energy is known in this disclosure as a neurostimulation signal, are well established in the medical literature and in other teachings, and will not be expounded upon here.

As stated above, the invention is also directed to an apparatus for neurostimulating a subject. The apparatus comprises a computing device that is operatively coupled to a neurostimulator, and a series of EEG sensors that are coupled to the neurostimulator. Examples of appropriate computing devices are microprocessors or computers. However, any processing unit can be used in the present invention as a computing device. These components are coupled to each other via electrical conduction paths. For example, the neurostimulator could be coupled to the computing device with RS232 cable, USB cable, etc. Further, the EEG sensors can be coupled to the neurostimulator with an electrical connector. However, in both instances, other methods of coupling the components are acceptable. The EEG sensors are configured (1) to be attached to the subject, (2) to monitor EEG signals of a subject, and (3) to administer neurostimulation signals to the subject. Additionally, the EEG sensors comprise at least one positive contact, at least one negative contact, and at least one ground contact.

The apparatus further comprises a biopotential acquisition device, at least one filtering unit, an isolation amplifier, and a microcontroller. A preferred microcontroller is the Toshiba TMP95FY64. However, any comparable microcontroller may be used. The biopotential device is operatively coupled to the computing device, and the neurostimulator is configured to transmit the biopotential data and EEG signal data to the biopotential acquisition device. These components may be coupled together in the manner set forth previously or in any additional manner that permits their correct usage. Additionally, the biopotential acquisition device is configured to transmit the EEG data and biopotential data through at least one circuit or numerical filter and through an isolation amplifier which is operatively coupled to the microcontroller. Furthermore, it is preferred that the isolation amplifier be capable of performing "notch" filtering (i.e., eliminate 60 Hz line noise) and it can be selected from any component found on the market. It is preferred that it be a Burr-Brown ISO-100.

It is preferred that the filtering unit be selected from the group consisting of a circuit configured to filter data and a numerical filter. It is also preferred that the biopotential acquisition device is a biopotential amplifier or a high resolution analog-to-digital converter.

The neurostimulator comprises a biopotential acquisition unit comprising an electric circuit configured to acquire biopotential data from the EEG signals obtained by the EEG sensors attached to the subject. The biopotential acquisition unit is also configured to analyze and store the acquired biopotential and EEG data with computational means and it is operatively coupled to the neurostimulator. The neurostimulator also comprises a transmission unit configured to transmit the biopotential and EEG data from the neurostimulator to the computing device and an I/O (input/output) unit configured to adjust for a time lag in the biopotential and EEG data being transmitted. The neurostimulator also comprises at least one switching unit configured to manage a neurostimulation signal.

It is preferred that the subject is a mammal. It is further preferred that the subject be a primate and even more preferred that the subject is a human being. It is also preferred that the switching device is a transistor.

Additionally, the neurostimulator comprises an inductor, acting as a transformer, whereas the stimulation signal is induced in the neurostimulator by inducing electrical current into the inductor, which further induces electrical current in the EEG sensors via electromagnetic coupling, and thereby into the subject.

The neurostimulator can further comprise an optical unit which further comprises a set of light generating devices located in close proximity to the pupils of the subject. It is preferred that the light generating devices are light-emitting diodes.

With reference to the accompanying FIG. 1, a preferred embodiment of the present invention is described where a computing device 8 is operatively coupled to a peripheral device henceforth referred to as a neurostimulator 9, such as through a peripheral cable 10. However, a peripheral cable is not the only method of coupling the neurostimulator to the computing device. The neurostimulator 9 further comprises a series of electrical conductors henceforth referred to as EEG sensors 11. The EEG sensors 11 consist of at least one positive lead 12, one negative lead 13 and one ground lead 14. However, the at least one positive lead 12, one negative lead 13, and one ground lead 14 may also be incorporated into one sensor as contacts.

In a preferred embodiment of the present invention, employing multiple sets of EEG sensors 11 simultaneously and multiple biopotential acquisition devices 15 can accomplish acquisition of EEG signals from multiple sites on the scalp. For clarity, the preferred embodiment is described with for acquisition of EEG signal from one scalp site. All EEG sensors 11 are connected to the neurostimulator 9 via EEG sensor connectors 17.

The neurostimulator 9 can further comprise, as a possible means of delivering the stimulation signal, an optical unit 16 that is electrically coupled to the neurostimulator 9 via optical device sensors connectors 19. The optical unit 16 can be connected to the neurostimulator 9 by an optical device cable 18. However, other means of connecting the optical unit to the neurostimulator are acceptable. The optical device further comprises light generating devices 20 located to be in close proximity to the subject's eyes. In the preferred embodiment, the light generating devices 20 are light emitting diodes 21.

The neurostimulator 9 is operated by any number of possible power supply 22 sources. To assure electrical isolation for the patient's safety, an isolated power supply 23 is utilized in the preferred embodiment. Further, the neurostimulator 9 is housed in a protective outer enclosure 24.

The neurostimulator 9 preferably internally comprises the biopotential acquisition device and the biopotential acquisition device is preferably designed to acquire biopotential data from EEG signal data, specifically patient EEG, to provide a means for analysis and data storage of the biopotential data through computational means, generate a neurostimulation signal and deliver the neurostimulation signal to the patient. It is preferred that a Teledyne A110-2 amplifier be used.

In a preferred embodiment of the present invention, EEG signals are acquired with EEG sensors 11 attached to a patient's scalp. At the end of the EEG sensors 11 attached to the patient are contact electrodes 25. The EEG signal is delivered to the neurostimulator 9 via the EEG sensors 11, connected to the biopotential acquisition device 15 through EEG lead connectors 17 and operatively coupled to a biopotential acquisition device 15 such as a biopotential amplifier or high resolution analog-to-digital converter. To minimize the effect of external electrical noise, any number of circuit or numerical filters 26 may be employed in the preferred embodiment. To assure patient safety, the biopotentials are passed through an isolation amplifier 27. The output of the biopotentials, after passing through the biopotential acquisition device 15, filters 26 and isolation amplifier 27 is acquired by a microcontroller 28 through analog-to-digital ports 29. The microcontroller 28 is operatively coupled to the computing device 8. One method of coupling the microcontroller to the computing device is to use a peripheral cable 10. Control of the neurostimulator 9 is accomplished by communication between the microcontroller 28 and the computing device 8. Further, the objective of biopotential data analysis and storage is accomplished computationally via communication between the microcontroller 28 and the computing device 8.

After analysis of the acquired biopotential, that is, the EEG signal, the computing device 8 communicates proper stimulation signal parameters, in accordance with the present invention, to the microcontroller 28. These parameters include signal energy level, frequency of the low frequency component of an AMPWM signal, phase offset of multiple signals, start time, frequency offset and duration through a user interface. Utilizing a digital-to-analog port 30 on the microcontroller 28, the stimulation signal is output from the microcontroller 28 to transistors 31 or similar switching devices capable of managing the current levels of the stimulation signal. Depending on the mode of stimulation chosen by a clinician, the stimulation signal will be routed to the different means of stimulation signal delivery, alone or in combination. The parameters for the clinician's choice are set forth above.

If optical stimulation is desired, the stimulation signal will be sent to the optical unit 16 featuring the light generating devices 20 to be worn by the patient. Any unit capable of emitting light may be used as a light generating device. This includes, but is not limited to a LED, a light bulb, a low-power laser, etc. Alternately, if EEG lead 11 stimulation is desired, where the stimulation signal is delivered to the patient's scalp via the attached electrodes 25, then the stimulation signal is sent to an inductor 32 which is designed to induce current in the EEG sensors 11 from the stimulation signal generated by the microcontroller 28. In the preferred embodiment of the present invention, a plurality of stimulation delivery modes is warranted to allow for clinician choice to further effect successful treatment based on individual patient needs.

To assure patient safety, all electronics in the neurostimulator 9, including the biopotential acquisition device 15, the filter 26, the isolation amplifier 27, the microcontroller 28 and the transistors 31 are supplied electricity by the aforementioned isolation power supply 23.

Finally, regarding the coupling of the components, if a computing device is used it is preferably operatively coupled to the processor of the neurostimulator via any of a number of means of commonly used peripheral communications techniques, such as serial communication, USB port communication or parallel communication 10. All remaining electronics are preferably operatively coupled to the processing device (e.g. microcontroller) in the neurostimulator. The data acquisition circuit preferably comprises the biopotential acquisition device 15, filters 26 and isolation circuitry (amplifier) 27. The isolation amplifier is preferably coupled to an analog-to-digital input port on the microcontroller 28, via electrical conduction paths such as wires or printed circuit board conductors. The filters 26 are preferably operatively coupled to the isolation amplifier 27 via electrical conduction paths such as wires or printed circuit board conductors. Further, the biopotential acquisition device 15 is preferably operatively coupled to the filters 26 via electrical conduction paths such as wires or printed circuit board conductors.

EEG leads 11 are preferably coupled to the biopotential acquisition device 15 via electrical connectors 17, providing conduction of EEG electricity at the scalp to the biopotential amplifier 15.

A stimulation circuit is preferably coupled to a digital-to-analog port 30 on the microcontroller, in all cases via electrical conduction paths such as wires or printed circuit board conductors. It is preferred that an isolated power supply 23 supplies all operative power for neurostimulation outputs such as that to the optical device 16 or the EEG lead stimulation inducing circuitry 32. Electrical output from the digital-to-analog port 30 is preferably conducted to a transistor 31 that is further coupled to the isolated power supply 23. When a signal is received at the base of the transistor 31 from the microcontroller 28, the transistor operates to switch on electricity from the isolated power supply 23 which is further conducted via electrical coupling to the inductor (stimulation inducing circuitry) 32. Current flow in the inductor 32 induces a current in the EEG lead, as described in the specification.

Alternately, for photic stimulation, the isolated power supply 23 is preferably coupled via electrical coupling to two more transistors 31, which are preferably operatively coupled via electrical coupling to independent digital-to-analog ports 30 on the microcontroller 28. Electricity conducted from the digital-to-analog ports 30 to the base of the transistors 31 in the photic stimulation circuit has the effect of switching on these transistors, further allowing for conduction of electricity to the photic stimulation devices, such as LEDs 21. The photic stimulation devices are preferably coupled to the transistors 31 via electrical connectors 19, thus providing for current flow to the photic stimulation devices such as LEDs 21.

Finally, it is preferred that the apparatus operate on a 12 volt power supply. It is more preferred that the apparatus operate on a 6 volt power supply. It is most preferred that the apparatus operate on a power supply equivalent to the lowest power supply requirement of the components used.

The following references are incorporated by reference in their entirety:
1. "High-frequency stimulation of the subthalamic nucleus silences subthalamic neurons: a possible cellular mechanism in Parkinson's Disease", Magarinos-Ascone C, Pazo J H Macadar O and Buno W. (Neuroscience 2002; 115(4): 1109-17.
2. "The spatial receptive field of thalamic inputs to single cortical simple cells revealed by the interaction of visual and electrical stimulation", Kara, Pezaris J S, Yurgenson S and Reid, R C. Proc Natl Acad Sci USA 2002 Dec. 10; 99(25): 16261-6.
3. "The anticonvulsant effect of electrical fields", Weinstein S, Curr Neurol Neurosci Rep 2001 March; 1(2):155-61.
4. "Electrical stimulation of the motor cortex in neuropathic pain", Tronnier V, Schmerz 2001 August; 15(4):278-9.
5. "Centromedian-thalamic and hippocampal electrical stimulation for the control of intractable epileptic seizures", Velasco M, Velasco F, Velasco A L, J Clin Neurophysiol 2001 November; 18(6):495-513

We claim:
1. A system for providing external electrical stimulation and treatment for a disorder by electrically stimulating and treating neurological tissue of a region of a brain, the system comprising:
means for generating an amplitude-modulated pulse-width modulation (AMPWM) signal, the AMPWM signal including a high frequency signal component and a low frequency signal component, wherein the high frequency signal component is amplitude-modulated and pulse-width modulated, wherein the high frequency signal component has a sufficiently high frequency to enable the AMPWM signal to penetrate high impedance portions of tissue located between external EEG sensors placed on a scalp and the neurological tissue of the region of the brain being stimulated, wherein the low frequency signal component is of sufficiently low frequency to provide the electrical stimulation and treatment, and wherein the low frequency signal component dynamically varies in frequency over time; and
means for transmitting the AMPWM signal from a neurostimulation device to the neurological tissue of the region of the brain being stimulated via the external EEG sensors placed on the scalp.

2. The system of claim 1, wherein the neurostimulation device and EEG sensors are externally located relative to the tissue and the neurological tissue of the region of the brain.

3. The system of claim 1, wherein the disorder to be treated is a neurological disorder.

4. The system of claim 1, further comprising means for simultaneously providing electrical stimulation and measuring of an overlapping voltage.

5. The system of claim 4, wherein the overlapping voltage is an electroencephalogram (EEG) signal.

6. A system for providing external electrical stimulation and treatment for a disorder by electrically stimulating and treating neurological tissue of a region of a brain, the system comprising:
a signal generator for generating an amplitude-modulated pulse-width modulation (AMPWM) signal, the generated AMPWM signal including a high frequency signal component and a low frequency signal component, wherein the high frequency signal component is amplitude-modulated and pulse-width modulated, wherein the high frequency signal component has a sufficiently high frequency to enable the generated AMPWM signal to penetrate high impedance portions of tissue located between external EEG sensors placed on a scalp and the neurological tissue of the region of the brain being stimulated, wherein the low frequency signal component is of sufficiently low frequency to provide the electrical stimulation and treatment; and
a transmission device coupled to the signal generator, wherein the transmission device transmits an electrical stimulation and treatment signal from the generated AMPWM signal, and wherein the transmitted electrical stimulation and treatment signal is communicated from the neurostimulation device to the neurological tissue of the region of the brain being stimulated via the external EEG sensors placed on the scalp to electrically stimulate and treat the disorder.

7. The system of claim 6, wherein the neurostimulation device and EEG sensors are externally located relative to the tissue and the neurological tissue of the region of the brain to be treated.

8. The system of claim 6, wherein the low frequency signal component dynamically varies in frequency over time.

9. The system of claim 6, wherein the disorder to be treated is a neurological disorder.

10. The system of claim 6, wherein the electrical stimulation and treatment signal includes an external stimulation signal that drives an external stimulation device.

11. The system of claim 10, wherein the external stimulation device is an audio stimulation device.

12. The system of claim 10, wherein the external stimulation device is an optic stimulation device.

13. The system of claim 10, further comprising:
a processor coupled to the signal generator, the processor being capable of controlling the signal generator.

14. The system of claim 13, further comprising:
a sensor coupled to the processor, the sensor being capable of receiving information from at least one reference site of the tissue located between the neurostimulation device and the neurological tissue of the region of the brain being stimulated, wherein information from the sensor is a parameter in determining the AMPWM signal.

15. The system of claim 14, wherein the sensor coupled to the processor is a lead for the neurostimulation device that transmits the electrical stimulation.

16. The system of claim 15, wherein the sensor coupled to the processor and the lead for the transmission is the electroencephalogram (EEG) sensor.

17. The system of claim 15, wherein the system is capable of simultaneous electrical stimulation and receipt of information from the at least one reference site of the tissue located between the neurostimulation device and the neurological tissue of the region of the brain.

18. The system of claim 14, wherein the sensor is capable of receiving electroencephalogram (EEG) information.

19. The system of claim 1, wherein the high frequency signal component is in the range of 43 hertz to 1,000,000 hertz and the low frequency signal component is in the range of 1 hertz -43 hertz.

20. The system of claim 19, wherein the high frequency signal component is in the range of 1,000 hertz -100,000 hertz.

21. The system of claim 19, wherein the high frequency signal component is in the range of 10,000 hertz -20,000 hertz.

22. The system of claim 6, wherein the high frequency signal component is amplitude-modulated and pulse-width modulated so as to control a time-averaged current of the AMPWM signal when passing through a conducting medium, wherein the conducting medium comprises the tissue located between the external EEG sensors placed on the scalp and the neurological tissue of the region of the brain being stimulated.

* * * * *